US009962556B2

(12) United States Patent
Dilmanian et al.

(10) Patent No.: US 9,962,556 B2
(45) Date of Patent: May 8, 2018

(54) RADIATION THERAPY WITH SEGMENTED BEAMS OF PROTONS AND OTHER IONS

(71) Applicants: BOARD OF REGENTS, THE UNIVERSITY OF TEXAS SYSTEM, Austin, TX (US); Avraham Dilmanian, Yaphank, NY (US); Sunil Krishnan; John Eley, Baltimore, MD (US)

(72) Inventors: F. Avraham Dilmanian, Yaphank, NY (US); Sunil Krishnan, Houston, TX (US); John Eley, Baltimore, MD (US)

(73) Assignee: BOARD OF REGENTS, THE UNIVERSITY OF TEXAS SYSTEM, Austin, TX (US)

(*) Notice: Subject to any disclaimer, the term of this patent is extended or adjusted under 35 U.S.C. 154(b) by 29 days.

(21) Appl. No.: 15/318,581

(22) PCT Filed: Jun. 24, 2015

(86) PCT No.: PCT/US2015/037550
§ 371 (c)(1),
(2) Date: Dec. 13, 2016

(87) PCT Pub. No.: WO2015/200559
PCT Pub. Date: Dec. 30, 2015

(65) Prior Publication Data
US 2017/0128739 A1 May 11, 2017

Related U.S. Application Data

(60) Provisional application No. 62/025,776, filed on Jul. 17, 2014, provisional application No. 62/018,030, filed on Jun. 27, 2014.

(51) Int. Cl.
A61N 5/06 (2006.01)
A61N 5/10 (2006.01)
G21K 5/04 (2006.01)

(52) U.S. Cl.
CPC .............. *A61N 5/06* (2013.01); *A61N 5/1045* (2013.01); *A61N 2005/1087* (2013.01)

(58) Field of Classification Search
CPC . A61N 5/06; A61N 5/1045; A61N 2005/1087
(Continued)

(56) References Cited

U.S. PATENT DOCUMENTS 8,269,198 B2   9/2012 Dilmanian et al.
2004/0162457 A1* 8/2004 Maggiore ............... A61N 5/10
                                                       600/1
(Continued)

OTHER PUBLICATIONS

Dilingham et al., "Interleaved Carbon Minibeams: An Experimental Radiosurgery Method with Clinical Potential," Int'l Jnl. of Radiation Oncology Biology Physics, 84:2 (Oct. 1, 2012), pp. 1-2.
(Continued)

*Primary Examiner* — Nicole Ippolito
(74) *Attorney, Agent, or Firm* — BKDowd Law, P.C.; Betsy Kingsbury Dowd

(57) ABSTRACT

A method for delivering therapeutic light ion radiation to a target volume of a subject, wherein the target volume is located at a predetermined depth from the skin, includes irradiating a surface of the skin with an array of light ion minibeams comprising parallel, spatially distinct minibeams at the surface in an amount and spatially arranged and sized to maintain a tissue-sparing effect from the skin to a proximal side of the target volume, and to merge into a solid beam at a proximal side of the target volume. A gap between the parallel, spatially distinct minibeams at the surface and a species of light ions forming the minibeams are selected such that the array merges into a solid beam at a predetermined beam energy, and across all energies for Bragg-peak spreading, at a proximal side of the target volume.

20 Claims, 7 Drawing Sheets

(58) Field of Classification Search
USPC ........ 600/1; 250/492.1, 492.2, 492.3, 396 R, 250/397
See application file for complete search history.

(56) References Cited

U.S. PATENT DOCUMENTS

| | | |
|---|---|---|
| 2007/0034812 A1 | 2/2007 | Ma et al. |
| 2008/0192892 A1* | 8/2008 | Dilmanian ............ A61N 5/1045 378/65 |
| 2008/0234531 A1* | 9/2008 | Welch ...................... A61N 5/10 600/2 |
| 2010/0034357 A1 | 2/2010 | Svesson et al. |
| 2010/0187446 A1 | 7/2010 | Dilmanian et al. |
| 2010/0327188 A1 | 12/2010 | Bert et al. |
| 2012/0330086 A1 | 12/2012 | Lidestri |
| 2013/0208867 A1* | 8/2013 | Beckman ............. A61N 5/1077 378/65 |
| 2016/0128983 A1* | 5/2016 | Djonov .............. A61K 41/0038 423/413 |

OTHER PUBLICATIONS

Int'l Search Report and Written Opinion for Int'l PCT/US2025/037550, dated Aug. 8, 2016.

\* cited by examiner

RADIATION THERAPY WITH SEGMENTED BEAMS OF PROTONS AND OTHER IONS

CROSS-REFERENCE TO RELATED APPLICATIONS

This application is a U.S. national phase filing of Int'l Application Ser. No. PCT/US15/37550, with an international filing date of Jun. 24, 2015, which claims the benefit of and priority to U.S. Provisional Application Ser. No. 62/018,030, filed Jun. 27, 2014, and to U.S. Provisional Application Ser. No. 62/025,776, filed Jul. 17, 2014, each of which is entitled "RADIATION THERAPY WITH SEGMENTED BEAMS OF PROTONS AND OTHER IONS," the entirety of each of which is hereby incorporated herein by reference thereto.

FIELD OF THE DISCLOSURE

The present invention relates to methods for performing minibeam radiation therapy for treating tumors, neurological targets, and other diseases, and, particularly, to methods of delivering therapeutic segmented beams of protons and other ions, particularly, light ions.

BACKGROUND

Proton therapy has become a significant radiation therapy around the world with more than ten facilities currently operating in the United States alone and several more in the making. Furthermore, although other light ions, e.g., deuterons, tritons, He-3 and He-4 ions, Li-6 and Li-7 ions, and ions of beryllium and boron, have not been used for radiation therapy, several types of accelerators currently used for proton and carbon therapy are capable of accelerating such light ions. Finally, radiation therapy with carbon ions, although not in clinical use in the United States yet, has been in clinical use in Japan and Germany for close to 15 years.

As used herein, the term "charged particles" refers generally to ions of elements from the periodic table of elements, of any atomic number.

In addition, the term "particle therapy," as used herein, refers to radiation therapy using any charged particle or ion.

While the term "light ions" may be used to refer to any ions or charged particles from protons to neon (from Z=1 to 10 inclusive), the methods of the present disclosure are particularly suited for ions and charged particles from protons to boron.

The advantages of light ions for radiation therapy over x-rays and gamma rays used in conventional radiation therapy are mostly their Bragg peak feature of dose deposition in tissues that allows better confinement of the dose to the target, as depicted in FIG. 2. FIG. 1 compares the dose deposition 10 with depth in tissues 12 of protons and carbon ion beams with that of high energy x-rays called MV x-rays because they are produced by MV electrons linacs. Proton therapy and carbon therapy of tumors are implemented by spreading the Bragg peak 14 to produce a flat dose 16 over the length of the tumor with only little exit dose (FIG. 2). Representative plots showing the Bragg peak for different energies 14 of carbon ions are shown as an example in FIG. 2, along with the resultant flat dose 16 resulting from Bragg-peak spreading across the energies. However, protons, carbons, and other charged heavy particles have a major disadvantage over MV x-rays and gamma rays used in Gamma Knife and that is that they do not have the sparing effect of the shallow tissues of the MV x-rays and gamma rays, an effect loosely called "skin-sparing effect", which is demonstrated in FIG. 1 as a large dip in the entrance dose of MV x-rays. Therefore, despite the fact that the Bragg-peak-spread dose protons and carbons deliver to the target is larger than their entrance doses, their entrance dose is still much higher than that of MV x-rays and gamma rays. This limitation of protons, carbon ions, and particle beams in general, combined with the very high radiosensitivity of the skin and certain other shallow tissues, such as the brain's frontal cortex, as described below, limits the entrance dose in each therapy session from these particles as compared to possible entrance doses from MV x-rays and gamma rays. Therefore, in contrast to MV x-rays and gamma rays that, depending on the size of the target, can be given in a single session (called single dose fraction) or just a few sessions, proton therapy is mostly administered in 20 to 30 dose fractions, which would be four to six weeks of five treatments each week. Although the number of dose fractions used in carbon therapy is generally smaller because of the high relative biological effectiveness (RBE) of carbon ions, which is mostly at their Bragg Peak, it still ranges from 5 to 15 because of their above lack of sparing effect of shallow tissues.

The sparing effect in shallow tissues by MV x-rays and gamma rays is well known, and is a result of the mechanism by which the dose is deposited. Being neutral particles, the x-rays and gamma rays deposit a dose by setting electrons in motion via either the photoelectric effect, Compton scattering, or pair-production, which in turn deposit the dose in tissue. For MV x-rays, Compton scattering is the dominant mode of interaction with tissues. The population of the electrons set in motion by the incident x-rays is built up only gradually, and typically it takes a centimeter or so for the built-up electron density to reach the equilibrium state. The depth and the shape of the "tissue sparing curve" of MV x-rays depend on the energy of the MV x-rays or gamma rays. It ranges from several millimeters for 6 MV linacs to about 15 mm for the 18 MV ones (FIG. 1). In that regard the curve in FIG. 1, made for 21 MeV x-rays, is highly atypical and is therefore exaggerated for our discussion.

On the other hand, protons, being charged particles, start depositing their energy into tissue immediately as they enter it. Accordingly, there is no such shallow tissue-sparing effect as there is for MV x-rays and gamma rays. This limits the entrance dose from these particles in comparison to possible entrance doses of MV x-rays and gamma rays.

Accordingly, there is a need for an effective radiation therapy using protons or other ions, particularly light ions, which advantageously confines the radiation dosage to the target, and that also offers shallow tissue and skin-sparing.

SUMMARY

Features of the disclosure will become apparent from the following detailed description considered in conjunction with the accompanying drawings. It is to be understood, however, that the drawings are designed as an illustration only and not as a definition of the limits of this disclosure.

The present disclosure relates to a system and methods for providing an effective radiation dose, using proton or other light ions, to a confined target volume, with a shallow tissue-sparing effect that allows for a higher entrance dose and consequently a higher therapeutic dose at the target.

The present disclosure is also directed to a method for delivering therapeutic light ion radiation to a target volume of a subject, wherein the target volume is located at a predetermined depth, the predetermined depth being measured from an irradiated portion of the surface of the skin of the subject. The method includes selecting a species of light ions for forming an array of minibeams directed at the target volume based on the predetermined depth. The method further includes selecting a predetermined energy of the selected species of light ions for confining the therapeutic radiation within the target volume such that the Bragg peak corresponding to the predetermined energy of the species is at a distal side of the target volume. The therapeutic radiation is delivered to the target volume by forming the array of minibeams, which are comprised of the species of light ions at the predetermined energy, and directing the array at the target volume. A portion of the surface of the skin is irradiated with the array of minibeams. The minibeams are arranged as parallel, spatially distinct minibeams at the surface of the skin in an amount and spatially arranged and sized to maintain a tissue-sparing effect from the surface of the skin to a proximal edge of the target volume and to merge into a solid beam at the proximal edge of the target volume.

The species of light ions is selected such that the minibeams broaden and merge into the solid beam at the proximal edge of the target volume to deliver a therapeutic dose of radiation to at least a portion of the target volume. Forming the array further includes selecting a gap between adjacent minibeams in the array to maintain the solid beam at the predetermined energy of the selected light ions at the proximal edge of the target volume.

In one aspect, the step of delivering the therapeutic dose further includes spreading the Bragg-peak of the light ions forming the minibeams by stepwise adjusting the predetermined energy of the light ions across a range of energies to produce a uniform dose distribution throughout the target volume. The step of selecting the gap includes selecting the gap for which the solid beam is maintained at the proximal edge for each of the energies across the range of energies.

In some aspects, the light ions forming the minibeams are protons.

In aspects, the array of light ion minibeams is a two-dimensional array of pencil minibeams.

In additional aspects, the method includes shaping a cross-section of the two-dimensional array to substantially match a cross-sectional shape of the target volume.

In yet additional aspects, the species of light ions for forming the minibeams are selected from the group consisting of protons, deuterons and ions of helium, lithium, beryllium, and boron.

In other aspects, the species of light ions for forming the minibeams are selected from the group consisting of deuterons and ions of helium, lithium, beryllium, and boron.

A cross-sectional profile of at least one of the light ion minibeams, in various aspects, has one of a circular, square, rectangular, elliptical, and polygonal shape. In yet additional aspects, the cross-sectional profile of each of the light ion minibeams has a substantially radially symmetrical shape.

In aspects, the method further includes providing a light ion source and a collimator downstream of the light ion source for forming the array.

In further aspects, the collimator is spaced apart from the surface of the skin for forming the array of light ion minibeams.

In various aspects, a width of each of the light ion minibeams at the surface is between 0.1 mm and 0.6 mm.

In some aspects, the width of each minibeam at the surface is about 0.3 mm.

In some additional aspects, the width of each minibeam at the surface is between about 0.1 mm and 1.0 mm.

In additional aspects, a gap between the minibeams at the surface is between about 0.1 mm and about 3.0 mm.

In some aspects, the gap between the minibeams at the surface is between about 0.1 mm and about 1.0 mm.

In another aspect, the light ions forming the minibeams have energies between 10 MeV per nucleon and 1000 MeV per nucleon.

In still other aspects, the array of light ion minibeams is a one-dimensional array of planar minibeams.

Some aspects of the method further include performing the additional steps of selecting a species of light ions, selecting a predetermined energy, and delivering the therapeutic radiation from a second direction, a second portion of the surface of the skin being irradiated from the second direction, the predetermined depth of the target volume being measured from the second portion of the skin.

The step of delivering the therapeutic dose from the second direction further includes, in aspects, spreading the Bragg-peak of the selected light ions forming the minibeams on the second portion of the skin by stepwise lowering the predetermined energy across a range of energies to produce a uniform dose distribution throughout the target volume. The gap between adjacent minibeams of an array irradiating the second portion is selected so that a solid beam is maintained at a proximal edge relative to the second direction for each of the energies across the range of energies.

The present disclosure is also directed to a method for delivering therapeutic light ion radiation to a target volume of a subject, wherein the target volume is located at a predetermined depth. The predetermined depth is measured from an irradiated portion of the skin of the subject. The method includes irradiating a portion of a surface of the skin with an array of light ion minibeams comprising parallel, spatially distinct minibeams at the surface in an amount and spatially arranged and sized to maintain a tissue-sparing effect from the surface of the skin to a proximal side of the target volume, and to merge into a solid beam at the proximal side of the target volume. A gap between adjacent parallel, spatially distinct minibeams at the surface and a species of light ions forming the minibeams are selected based on a depth of the target volume from the surface.

In aspects, a species of light ions forming the light ion minibeams is selected from the group consisting of protons, deuterons, and ions of helium, lithium, beryllium, and boron.

In additional aspects, the method includes spreading the Bragg-peak of a predetermined energy of the species of light ions forming the minibeams by stepwise adjusting the predetermined energy of the light ions across a range of energies to produce a uniform dose distribution throughout the target volume. The species of light ions and the gap are selected so that the minibeams broaden and merge into the solid beam at the proximal side for each of the energies across the range of energies.

In additional aspects, the method can include raster-scanning an incident light ion radiation beam to form the array of light ion minibeams for irradiating the target volume.

In addition to the above aspects of the present disclosure, additional aspects, objects, features and advantages will be apparent from the embodiments presented in the following description and in connection with the accompanying drawings.

BRIEF DESCRIPTION OF THE DRAWINGS

The drawings constitute a part of this disclosure and include examples, which may be implemented in various forms. It is to be understood that in some instances, various aspects of the disclosure may be shown exaggerated or enlarged to facilitate understanding. The teaching of the disclosure can be readily understood by considering the following detailed description in conjunction with the accompanying drawings.

DETAILED DESCRIPTION

The following sections describe exemplary embodiments of the present invention. It should be apparent to those skilled in the art that the described embodiments of the present invention provided herein are illustrative only and not limiting, having been presented by way of example only. All features disclosed in this description may be replaced by alternative features serving the same or similar purpose, unless expressly stated otherwise. Therefore, numerous other embodiments of the modifications thereof are contemplated as filling within the scope of the present invention as defined herein and equivalents thereto.

It is noted that protons, and proton beam therapy, are treated separately from other radiation therapies in the prior art. To date, radiation beam therapy for other light ions is not known in the prior art. The present disclosure is directed to radiation therapies using both protons and other light ions. For simplicity, the terms "light ions" and "species of light ions" as used in the present disclosure include protons as well as deuterons and ions of helium, lithium, beryllium, and boron.

Figure 1:
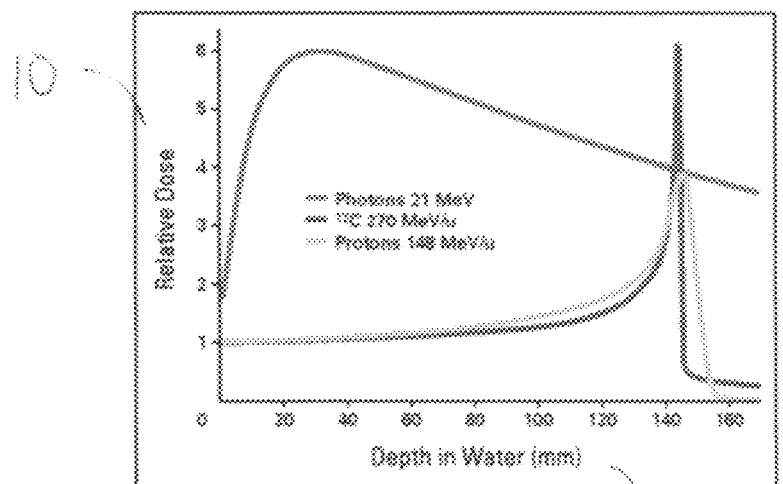
FIG. 1 is graph illustrating dose distributions in water from protons, carbons, and x-rays.
Figure 2:
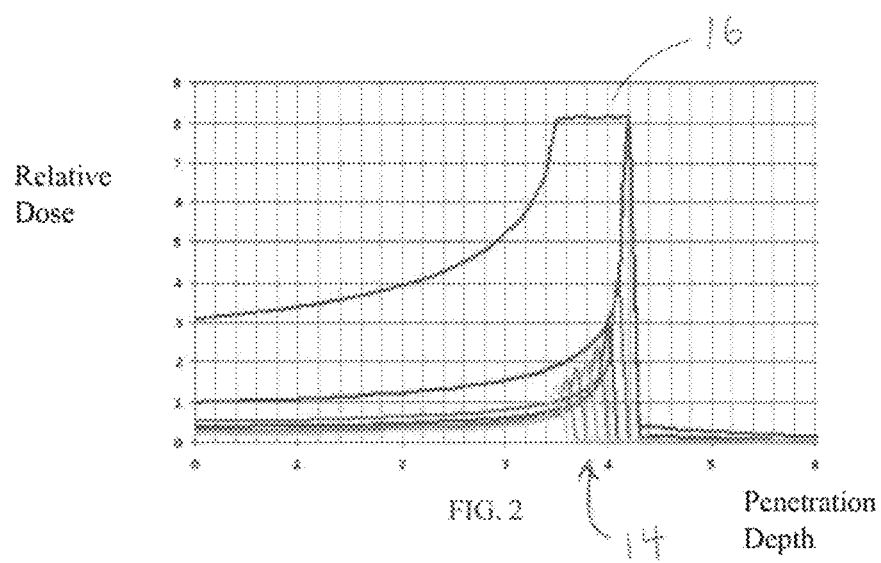
FIG. 2 is a graph illustrating a Bragg-peak spreading to produce a uniform dose at a target.
Figure 3:
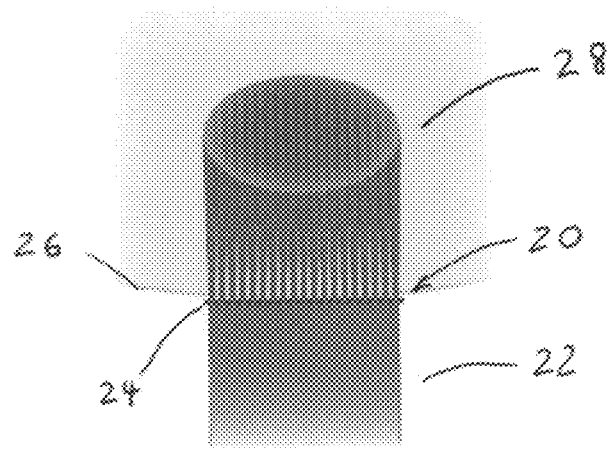
FIG. 3 is a pictorial representation of an embodiment of a two-dimensional array of parallel pencil beams of protons forming a circular cross-section formed in accordance with an embodiment of the present disclosure.

The present disclosure relates to a new solution to the problem of the lack of the sparing effect of skin and other shallow tissues in protons and other ions, particularly, light ions. Referring to FIG. 3, for example, in one embodiment, to deliver a therapeutic dose of radiation to a target volume which encompasses, for example, a tumor, incident, parallel beams 20 of ions of a predetermined species are formed, for example, by segmenting an incident radiation beam using a collimator 24 positioned on, or in front of, the surface 26 of the skin. The application of such an array spares the skin and the shallow tissues until they go above 0.7 mm size and/or merge with each other to produce a solid beam.

In some embodiments, the incident radiation can be segmented into an array of nearly parallel, small pencil beams 20 on the surface of the skin. In some embodiments, the minibeams formed in accordance with the present disclosure have a width (or diameter, in the case of circular pencil minibeams) between about 0.1 mm and about 0.6 mm. The cross-section of the pencil beams can be, but is not limited to, a circular, or nearly circular shape. In other embodiments, one or more of the pencil beams can be square, rectangular, elliptical, or polygonal in shape. One of ordinary skill in the art will appreciate that numerous other cross-sectional shapes can also be used.

Figure 4:
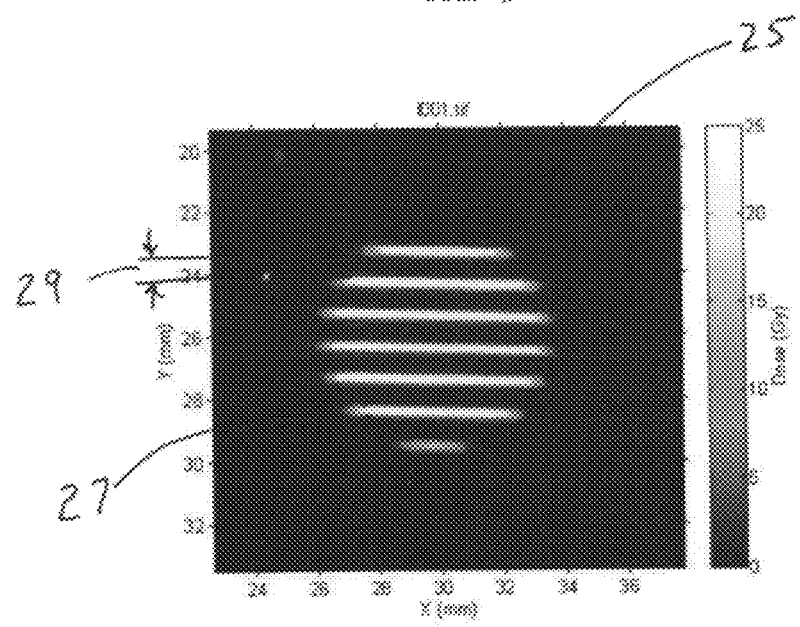
FIG. 4 is a pictorial representation of an embodiment of a one-dimensional array of proton planar minibeams formed in accordance with the present disclosure.

Referring also to FIG. 4, in some embodiments, the incident radiation can be segmented into an array of parallel, or nearly parallel, narrow planar minibeams 25 on the surface of the skin. In some embodiments, the planar minibeams have a width or thickness 27 of between about 0.1 mm and about 0.6-mm-diameter.

In particular embodiments, the minibeams have a width 27, or a diameter in the case of pencil beams, of about 0.3 mm.

The minibeams formed in accordance with the present disclosure are spaced sufficiently on the surface of the skin to spare the tissue between the minibeams as well as to form a solid or continuous beam at the desired target depth.

The spacing of the minibeams is described herein in terms of a gap between the edges of the minibeams. An on-center spacing between the minibeams may also be specified. One of ordinary skill in the art will appreciate that in such cases, the gap between the minibeams is determined by both the on-center spacing and the width or thickness (FWHM) of the minibeams.

In some embodiments, a gap 29 between the minibeams formed in accordance with the present disclosure is between about 0.1 mm and about 3.0 mm.

In other embodiments, a gap between the minibeams formed in accordance with the present disclosure is between about 0.1 mm and about 1.0 mm.

In still other embodiments, a gap between the minibeams formed in accordance with the present disclosure is between about 0.5 mm and about 0.8 mm.

In additional embodiments, a gap between the minibeams formed in accordance with the present disclosure is about 0.7 mm.

The application of the arrays of minibeams of the present disclosure, which can be pencil beams or planar beams, spares the skin and the shallow tissues until they go above 0.7 mm size and/or merge with each other to produce a solid beam.

The minibeams 20 shown in FIG. 3 can be pencil beams or planar beams. The size and spacing of the beams at the surface of the skin advantageously promote shallow tissue sparing from the skin to a proximal side of the target volume. As these individual beams penetrate the tissues they gradually broaden. For a known depth of the target volume from the surface, the gap between the minibeams and the particular species of ions forming the minibeams can be selected so that the minibeams merge with their neighbors to form a solid radiation field 28 at the target volume.

It is noted that the target volume is usually not confined only to a tumor, for example, but can also include a certain amount of tissue surrounding the tumor.

Referring to FIG. 4, in some embodiments, the array of parallel light ion minibeams of the present disclosure is a one-dimensional array of planar minibeams 25.

In some embodiments, a multislit collimator, for example, a tungsten multislit collimator, is used to produce an array of minibeams. For example, a tungsten multislit collimator was used to produce an array of 100 MeV planar proton minibeams with 0.3 mm width and 0.7 mm gaps between the planar minibeams. FIG. 4 shows the resulting pattern captured on a chromographic film, which was positioned at the downstream end of the collimator.

In other embodiments, the array of parallel light ion minibeams of the present disclosure is a one-dimensional array of pencil minibeams formed in accordance with the present disclosure.

Referring to FIG. 3, in other embodiments, the array of parallel light ion minibeams of the present disclosure is a two-dimensional array of pencil minibeams formed in accordance with the present disclosure.

In some embodiments, the depth at which the minibeams of the present disclosure merge is about 1 cm to about 3 cm.

In embodiments, the methods of the present disclosure are implemented to deliver therapeutic doses of radiation to brain tumors, including pediatric brain tumors.

The medical significance of the present method's sparing of the shallow tissues can be divided in the following categories. First, the effect spares the skin, which is a highly radiosensitive organ. This allows the use of higher incident particle doses than those possible today. As a result the dose given in each session (called dose fraction) can be increased and therefore the total number of dose fractions can be reduced, making the treatment easier on the patient. This reduction is called "hypofractionation." Second, the method will spare the brain's frontal cortex. Sparing of the frontal cortex is vital in reducing late cognitive effects in children and also in adults because it is a major site of generation of the brain's actively dividing neural stem cell (NSCs) that turn into glia, particularly oligodendrocytes (SP Rodgers et al., Neural Plasticity 2013; 698528). Oligodendrocytes are the cells that produce myelin, the coating of the axons. The process, called gliogenesis, introduces plasticity in the brain, particularly the pediatric brain. The need for new oligodendrocytes and new myelin are the most important feature of the brain particular the growing brain. This process also involves angiogenesis in the cortex. The preponderance of dividing cells makes the process highly radiosensitive. As a result, radiation damage to the pediatric frontal cortex produces a long-term decrement in cell proliferation. This cell decrement, together with the direct radiation effect on the neural cells, produces a neural environment that is hostile to plasticity. Furthermore, long-term suppression of cell proliferation deprives the brain of the raw materials needed for optimum cognitive performance, e.g., new glia in frontal cortex, while chronic inflammation and dearth of trophic substances, such as the above, limit neuroplastic potential in existing circuitry. Finally, the grey-matter layer of the cerebral cortex, which is rich with neurons and their dendrites, is also radiosensitive and is therefore another organ whose sparing by the present methods will reduce the depth of the neurological deficits caused by radiation in children and adults.

There is no known prior attempt to add skin-sparing effect to protons or light ions. One attempt to add skin-sparing effect to heavier ions, such as carbon ions, is described in U.S. Pat. No. 8,269,198 to Dilmanian et al. (the "'198 patent"), the entirety of which is incorporated herein by reference. In the '198 patent, some skin-sparing effect is achieved by interleaving carbon minibeams. The method has shown certain success in pre-clinical studies. However, it requires the tissues to be completely immobilized. Also, it requires much more expensive facilities than those of proton therapy.

The heavy ion beams of the '198 patent, while exhibiting some broadening, are able to be sufficiently shaped and controlled to form a solid beam at a desired target using the interleaving methods of the '198 patent. On the contrary, light ion beams, including proton beams, broaden too excessively to be suitable for interleaving, except for very shallow and very small targets.

In the present disclosure, the intersection of broadening light ion minibeams in an array forms a solid or continuous minibeam at a predetermined depth by carefully controlling the minibeam widths and the gap between arrays of minibeams. Accordingly, in contrast to prior methods known in the art, each array of minibeams formed in accordance with the present disclosure independently forms a solid or continuous beam of radiation at the target. No interleaving of multiple arrays is required to form the solid beam. In addition, because a solid beam of radiation can be delivered by each independent array, without interleaving arrays, the target volume can be irradiated with arrays of the minibeams formed in accordance with the present disclosure from any number of different directions, each aimed to strike the target volume.

It should be understood that while the embodiments described herein are directed to proton and light ion minibeams, the methods are not limited thereto. Accordingly, in some embodiments, the methods may include irradiation of a shallow target volume using two-dimensional arrays of heavier ion parallel pencil beams formed in accordance with the present disclosure.

In some embodiments, the incident radiation comprises one or more of protons, deuterons, and ions of helium, lithium, beryllium, and boron. In other embodiments, the incident radiation may comprise carbon ions.

Referring again to the embodiment of FIG. 3, in one embodiment, the incident beam 22 comprises protons and is converted into an array of nearly parallel proton pencil beams of 0.1 to 0.6 mm incident diameter using a multi-hole heavy-metal collimator 24 positioned on the patient's skin 26. The gaps between the holes in the collimator, depending on the clinical need, can be as small as 0.1 mm.

In other embodiments, the incident beam comprises one or more species of light ions.

It is estimated that the tissue-sparing effect of arrays of proton minibeams formed in accordance with the present disclosure starts to diminish when they are about ⅔ of the way to merge with each other. This is because just before they merge the gaps between them start to diminish, producing some "valley" dose between the minibeams. It has also been estimated that the full tissue-sparing effect will be about 10-fold above the tolerance of the tissue to solid beams of protons.

As the individual proton minibeams penetrate the tissue, they gradually broaden by multiple scattering off the electrons in their paths, and at some tissue depth, depending on the gap (or on-center spacing and beam width) between the beams, they merge with their neighbors to produce a solid proton beam. Also, as the individual minibeams broaden, they gradually lose their tissue sparing effect, with the nominal threshold for losing all their tissue-sparing effect having been found to be about 0.7 mm for the proton and light ion minibeams of the present disclosure. For this reason, the gap between the minibeam holes in the collimator is preferably adjusted so that the adjacent minibeams for a particular species of light ions merge with their neighbors either when they reach 0.7 mm in diameter, which would be a depth of about 30 mm from the skin, or before that, depending upon whether the target to be treated is farther from the skin than that or closer. In this way the target volume, which includes the tumor, receives a solid beam of protons, while the skin and the shallower tissues receive tissue-sparing beams.

In the system and methods of the present disclosure, a two-dimensional array of parallel minibeams of protons formed in accordance with the present disclosure, for example, can be arranged in any pattern to form a cross-sectional shape and size to match the cross-sectional shape and size of, for example, a tumor. As shown in FIG. 3, for example, the array of minibeams form a circular cross-section at the target volume. Accordingly, the present method is not limited to treatment of very small objects.

In one embodiment, at the surface of the skin where the array is formed, each minibeam has a width of ~0.3 mm. This is considerably smaller than the 0.7 mm beam diameter where the method's tissue-sparing effect starts to diminish.

In some embodiments, the width of each minibeam is between about 0.15 and 0.25 mm.

In other embodiments, the depth of the tissue in which the minibeams for a particular species of light ions merge is selected in accordance with the depth of the proximal side of a target volume that encompasses the tumor by adjusting the gap between the minibeams. Because of the approximate 0.7 mm diameter of the minibeams at which the tissue tolerance starts to diminish for a given proton (or other species of ion forming the minibeams) beam energy, the tissue depth for beam merging is preferably selected for depths at which the minibeams grow beyond 0.7-mm in diameter.

Figure 6:
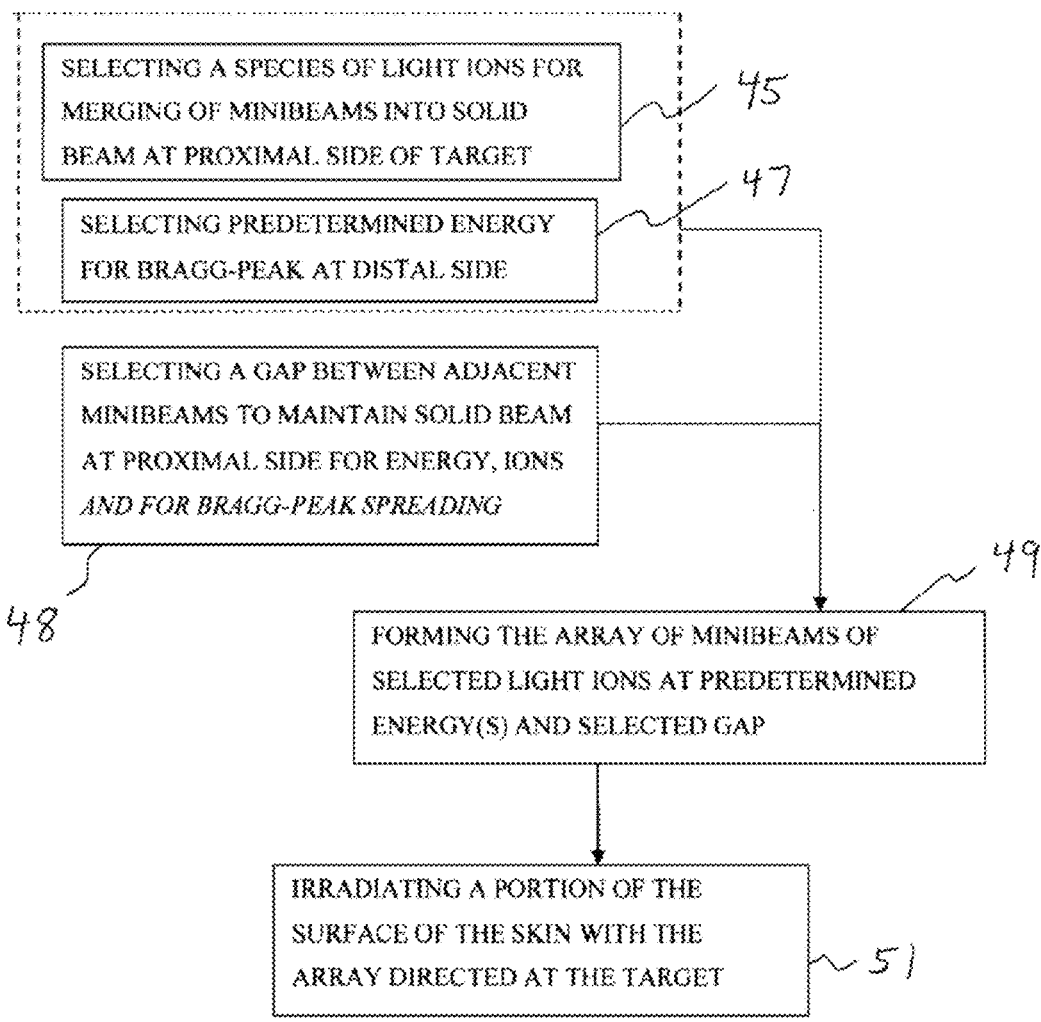
FIG. 6 is a representation of the steps of an embodiment of a method of the present disclosure.
Figure 10:
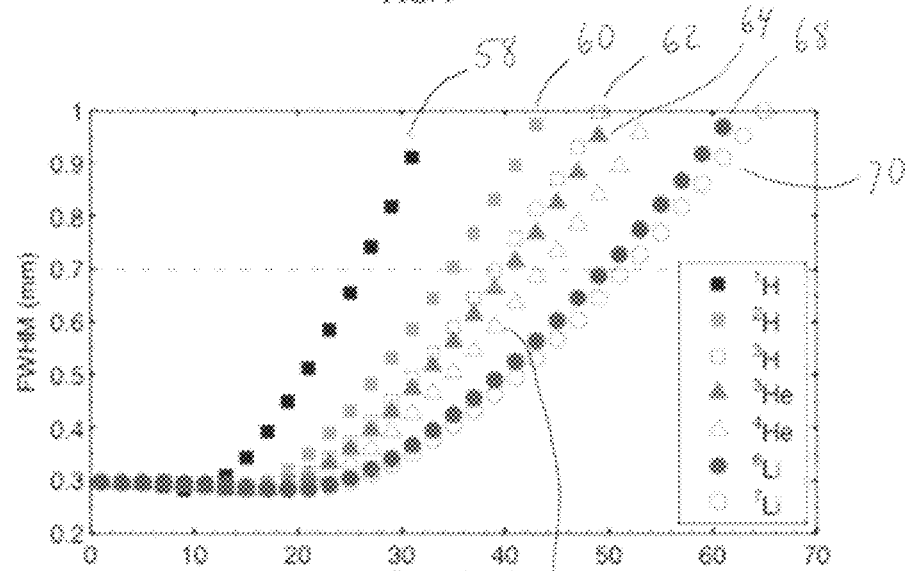
FIG. 10 is a graphical representation of the divergence in water of proton and light-ion minibeams formed in accordance with the present disclosure for a beam energy corresponding to approximate 10 cm Bragg-peak depth.

As illustrated in FIG. 6, an embodiment of the method of the present disclosure may include selecting a species of light ions, at 45, such that minibeams of a particular width (0.3 mm, for example) will merge at the proximal side of a target volume that encompasses the tumor. In embodiments, the gap between the minibeams is also set such that the beams merge at the same depth at which the minibeams broaden to about 0.7 mm width. As illustrated in FIG. 10, the ion species are characterized by different rates of broadening, so that the optimum selection is based on the depth of the proximal target location. In particular, the species of light ions is selected that provides an adequate rate of minibeam broadening so that minibeams, with proper beam spacing, merge by the time they reach the proximal side of the target, yet still provide tissue sparing along the path of the array from the skin surface to the proximal side of the target.

In embodiments of a method of the present disclosure, an energy of the light ions in the incident minibeams ("beam energy") irradiating the target volume is also selected based on a known depth within the target volume at which the light ions forming the minibeams will stop traveling. This depth can be calculated as the position of the well-known Bragg-peak, the depth at which the ions lose all their energy and at which the highest radiation dose is delivered. In the embodiment of FIG. 6, the method includes selecting a beam energy, at 47, for producing the array such that the Bragg peak occurs at a distal side of the target volume to confine the therapeutic dose of radiation to the target volume.

For the predetermined energy, a gap between the adjacent minibeams is also selected, at 48, such that the solid beam is maintained at the proximal side of the target. The gap between minibeams, the beam energy of the light ions, the species of the light ions, and the width of the minibeams, may each be adjusted within the various parameters described herein, to select the optimum parameters for forming an array of minibeams on the surface of the skin, at 49, which is directed at the target volume, to deliver a therapeutic solid (continuous) beam of radiation, at 51, substantially only to the target volume, and not to the surrounding tissue.

Embodiments of the method also include spreading the Bragg-peak of the light ions, at 48, by any means known in the art, to deliver a uniform dose of therapeutic radiation across the target volume. The maximum beam energy selected corresponds to the Bragg peak at the distal side of the target. By stepwise lowering the energy from the maximum energy, so that successive Bragg peaks occur from the distal to the proximal side of the target volume, a uniform dose distribution is provided throughout the depth of the target. Any known method of producing this Bragg-peak spreading can be used to produce a uniform dose distribution along the known depth of the target.

Accordingly, the method may further include, at 48, selecting the optimal gap between the minibeams for the species of light ions selected, such that the minibeams forming the array, at 49, merge into a solid beam at the proximal side of the target volume for every beam energy in the range of beam energies used for Bragg-peak spreading.

In some instances, a patient may be treated with radiation administered during the same session, or during different sessions, where each successive radiation treatment may be delivered to the tumor from a different direction. In embodiments of the present method, for each irradiation direction used to treat a patient, the target volume is preferably irradiated across the range of predetermined energies, as described supra, to produce a uniform dose by Bragg-peak spreading.

Figure 5A:
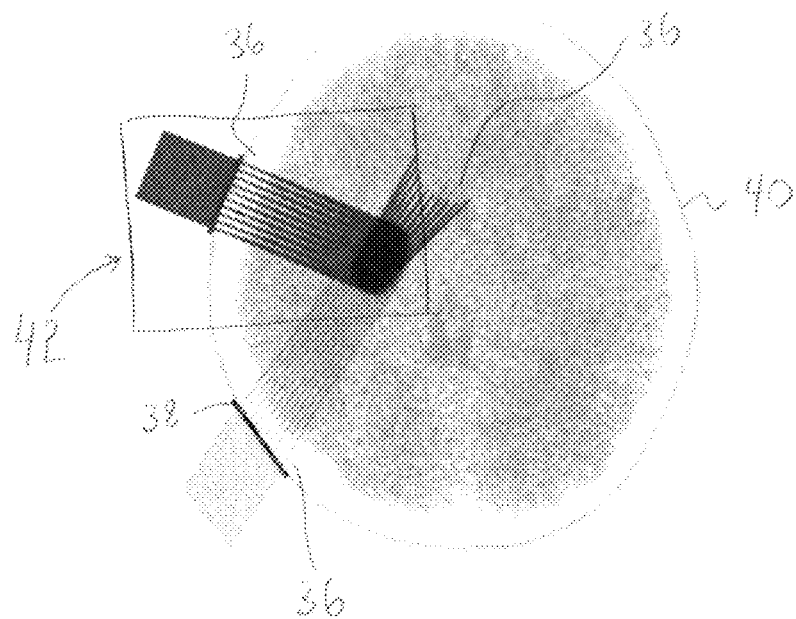
FIG. 5A is a schematic representation of an embodiment of a method of treating a brain tumor with proton minibeams in accordance with the present disclosure.
Figure 5B:
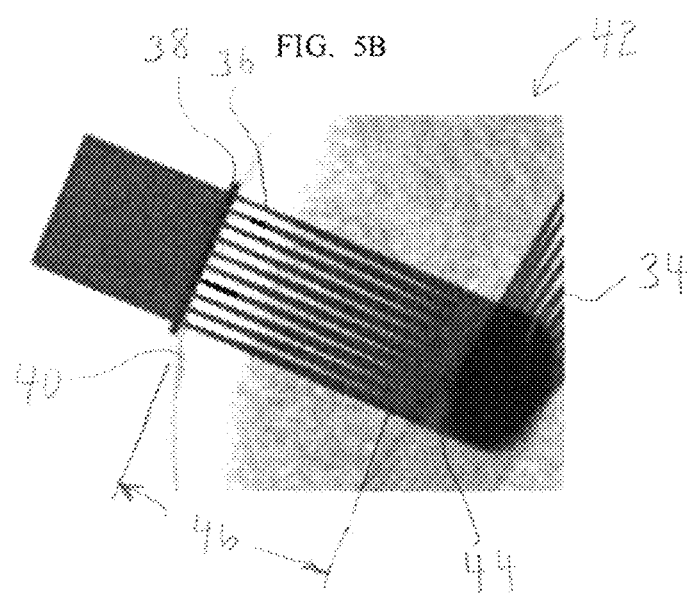
FIG. 5B is a schematic representation of a magnified section of part of FIG. 5A.

FIG. 5A shows a schematic view of a brain tumor 34 being irradiated by a method formed in accordance with the present disclosure, including irradiating the brain tumor from three directions with minibeam arrays 36, with a collimator 38 appropriately positioned on the surface of the skin 40 for each irradiation. Each irradiation is performed across different beam energies selected in accordance with the present disclosure to confine the radiation dose within the target volume and to deliver a uniform dose across the target, using the Bragg-spreading effect. The distance of the target volume from the irradiated surface of the skin differs for each of the radiation angles shown. In accordance with the method of the present disclosure, for each of the different radiation angles, the selected range of beam energies for producing a uniform dose, and the corresponding optimal gap and species of light ions are adjusted in accordance with the distance of the proximal and distal side of the target volume from the irradiated surface of the skin. FIG. 5B shows the magnified view 42 of one of the arrays of minibeams providing one of the three irradiation exposures of FIG. 5A.

The target volume can be irradiated with arrays of the minibeams formed in accordance with the present disclosure from any number of different directions, each aimed to strike the target volume. It should be noted that, for each direction, the ion species and/or the gap between the minibeams should be adjusted so that the minibeams merge into a solid or nearly solid beam near the proximal side of a therapy target. The tissue depth of the proximal side of the target from the surface of the skin, and thus the depth at which the minibeams should merge, will, of course, most likely differ for each irradiation angle.

As shown in FIGS. 5A and 5B, the minibeams, which were about 0.3 mm in beam width (FWHM) at the surface of the skin, preferably merge together at the proximal side 44 of the target volume encompassing a tumor, for example (before or at the proximal side of a tumor), and at a tissue depth 46 where the minibeams become 0.7 mm or larger in diameter, which is at ~2.5 cm. The merging should not be deeper than 2-cm because this would mean that the minibeam spacing on-center will be larger than 0.7 mm, which will reduce the rate of delivered dose to the target.

For 0.7-mm on center spacing, the ratio between the dose rate reaching the target from a solid proton beam and that from minibeams for the same incident beam intensity is 7:1, which is calculated by dividing the area of a square with 0.7 mm side to that of a circle with 0.3 mm diameter. For example, for 0.9 mm on-center spacing that ratio becomes 11.5:1, which means much beam is wasted. In fact the on-center spacing is preferably smaller than 0.7 mm for a target closer than ~2.5 cm to the surface. Finally, the subject should be completely immobilized through the irradiation times. In this regard, it is noted that the brain's cardiosynchronous brain pulsation, which can be 0.3 mm or larger in adults, is expected to be smaller in children.

In an embodiment of a system of the present disclosure, a quadrupole magnetic lens is used to focus raster-scanned beams of light ions produced by a source, such as a synchrotron source, to a very narrow width only at the patient surface and simultaneously introduce angular spread in the beams so that they broaden as they approach the target volume, e.g., the cancer target depth.

In another embodiment of a system formed in accordance with the present disclosure, a scattering foil is placed on the downstream surface of a pinhole collimator to introduce angular confusion in the individual minibeams, so that the beams of light ions have very narrow width at the patient surface and broaden to converge into a broad beam, as they approach the target volume encompassing, for example, a cancerous tumor.

In another embodiment of a system and method of the present disclosure, a gap is introduced between the collimator producing the array of parallel minibeams and the skin. The frame used for this purpose can push on the skin instead of the collimator for patient immobilization. The introduction of a 5-cm gap between a collimator producing an array of planar proton minibeams of 0.3 mm FWHM thickness, with 1.0 mm spacing on-center, was shown to reduce the skin dose from neutrons produced in the collimator by 7 fold compared to the skin dose that occurs when the collimator is resting on the skin.

In embodiments, the collimator producing the array of parallel minibeams of the present disclosure is spaced from the skin by about 5 cm, or between about 2.5 cm and about 5 cm from the skin.

In other embodiments, the collimator is spaced from the skin by between about 2.0 cm and 6.0 cm of the skin.

EXPERIMENTAL RESULTS & SIMULATIONS

Figure 7:
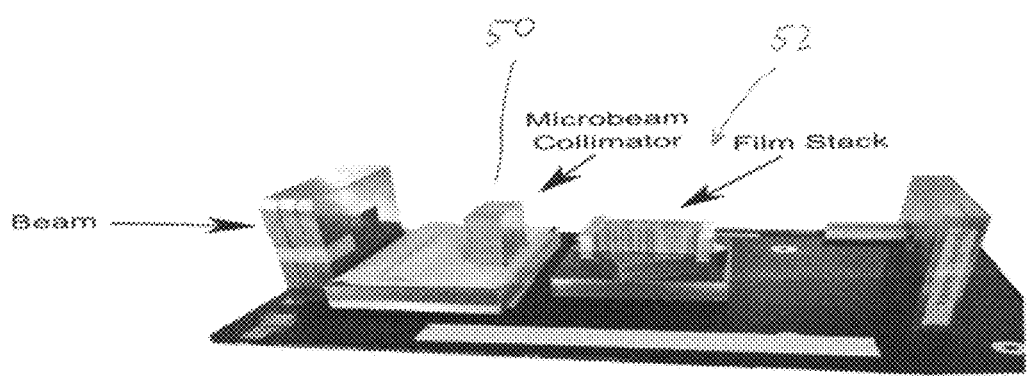
FIG. 7 is a schematic representation of an experimental set-up for measuring divergence of minibeam of the present disclosure.
Figure 8:
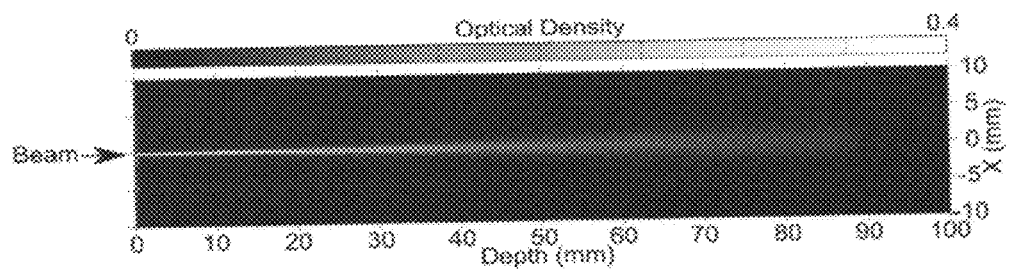
FIG. 8 is a graphical representation showing results of the experiment illustrated in FIG. 7.

Measuring the Divergence of Pencil Minibeams Formed in Accordance with the Present Disclosure Produced with a 150-MeV Proton Minibeam:

A 0.3 mm collimator 50 was positioned in the way of a 150-MeV proton beam. Next, a stack of chromographic films 52 was positioned in front of the beam with 2-mm plastic sheets between the adjacent films. The experimental set-up is depicted in FIG. 7, while the results are presented in FIG. 8. Quantitative analysis of the results of FIG. 8 shows that the 0.3 mm proton minibeams broaden to ~1.3 mm FWHM at 50 mm plastic depth. This is close (namely 1.24 mm) to what was observed with Monte Carlo simulations using Monte Carlo N-Particle extended (MCNPX) code.

Figure 9:
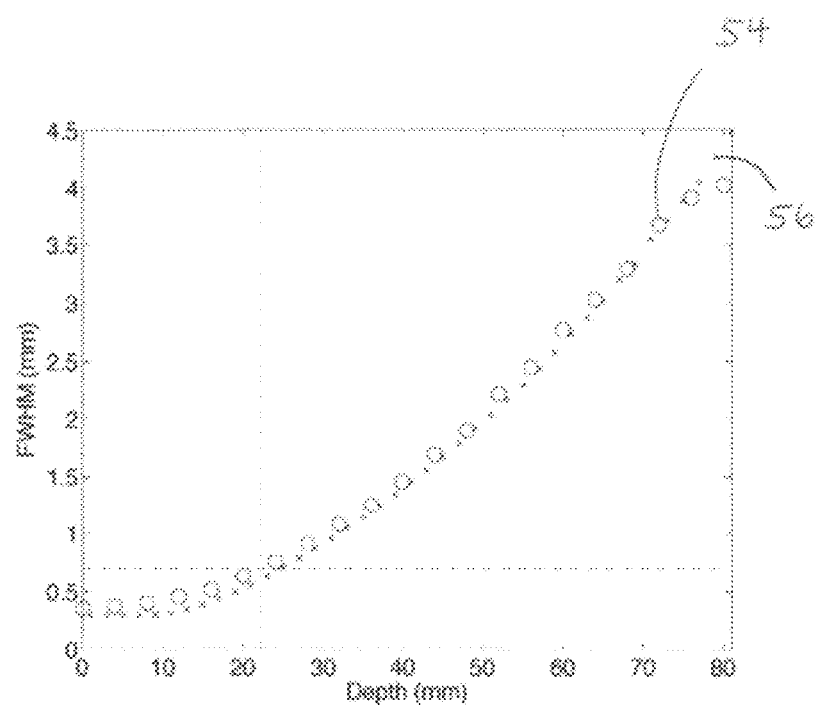
FIG. 9 is a graphical representation showing divergence as a function of depth in water of proton minibeams formed in accordance with the present disclosure at 109 MeV beam energy.

Measuring and Simulating the Beam Divergence of Pencil Minibeams of 109 MeV Protons:

The above measurement of FIGS. 7 and 8 were repeated using 109 MeV protons, which is closer to the beam energy used for treating brain tumors. FIG. 9 compares the experimental results (circles) 54 with those from MCNPX simulations in water (x marks) 56. The match is very good. The results show that the water depth where the beam reaches 0.7 mm FWHM is about 2.5 cm.

Simulating the Beam Divergence of the Pencil Minibeams for Several Light Ions Compared to Protons:

The code MCNPX was also used to calculate the divergence of 0.3-mm pencil minibeams made of protons 58 and several other light ions formed in accordance with the present disclosure, namely H-2 60, H-3 62, He-3 64, He-4 66, Li-6 68, and Li-7 70 in water (FIG. 10). The results clearly show the trend of smaller beam divergence for particles of larger mass and larger atomic number. This is a most significant effect because it indicates that the heavier particles reach the 0.7 mm diameter (FWHM) at larger tissue depth than the approximate 26 mm depth measured for protons (see FIG. 10, plot 58). As a result, in some embodiments formed in accordance with the present disclosure arrays of parallel minibeams made of these light ions can be used to spare a larger depth of the shallow tissues. According to FIG. 10, for minibeams of protons and the light ions listed above, these tissue depths are approximately 26, 34, 39, 41, 43, 49, and 51 mm, respectively. For arrays of planar minibeams of 0.3 mm FWHM, the protons and light ions were found to reach the 0.7 mm FWHM at depths of 1 to 2 mm longer. The beam energies used for these particles, the beam energies being chosen for producing Bragg peaks at approximately 10 cm water depth, were 109, 157, 188, 410, 462, 873, and 931 MeV, respectively. Ten million particle histories were tracked for each ion species.

Figure 11A:
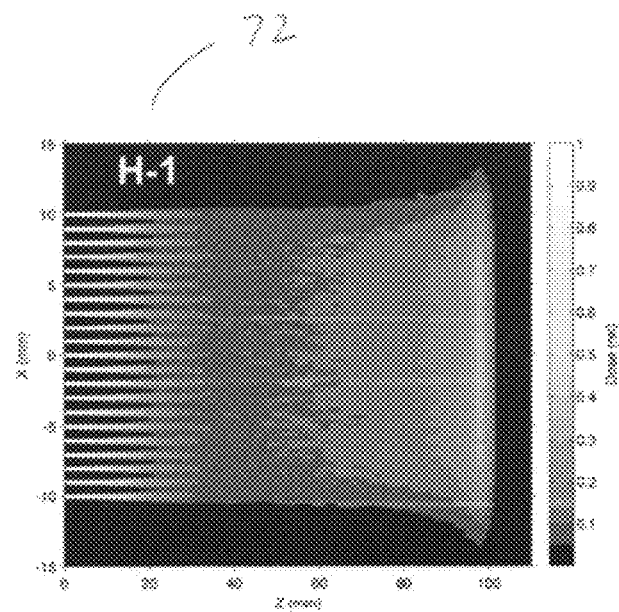
FIG. 11A is a graphical representation of the divergence of minibeams in water for arrays of parallel proton minibeams formed in accordance with an embodiment of the present disclosure.
Figure 11B:
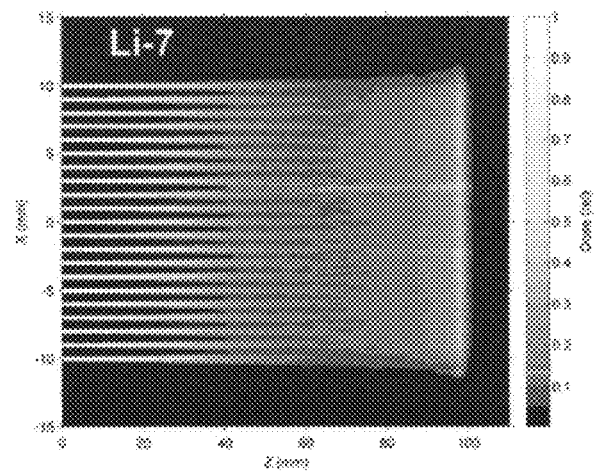
FIG. 11B is a graphical representation of the divergence of minibeams in water for arrays of parallel Li-7 minibeams formed in accordance with an embodiment of the present disclosure.

Simulating the Beam Divergence for Entire Arrays of Proton and Li-7 Pencil Minibeams:

Referring to FIGS. 11A and 111B, Monte Carlo simulations of absorbed dose from 2-dimensional pencil minibeam arrays composed of 116-MeV proton beams 72 and 931-MeV lithium-7 beams 74, producing Bragg peaks at 10 cm water depth, were performed. The arrays consisted of 21×21 minibeams, spaced on a 1-mm grid (1.0 mm on-center spacing), each having an initial circular cross section with 0.3-mm diameter (FWHM). No Bragg-peak spreading was carried out. These data support the above concept that heavier light ions allow sparing of deeper proximal tissues to the target than protons because of their smaller divergence. This makes the technique of selecting the right light-ion-species for each individual patient treatment, in addition to selecting the beam geometry including the thickness and separation gap, a most powerful aspect of this method.

Dosimetry Results for Various Beam Geometries and Ion Species:

As described herein, the ion species and beam geometries (spacing and thickness of planar or pencil beams) are optimized for a particular beam energy to enhance tissue sparing while delivering appropriate dose to a tumor in accordance with the present disclosure. The results of a MCNPX simulation for three (3) different target geometries using 0.3-mm planar beams are shown in Tables 1 and 2 below. The ion species was chosen on the basis of the depth of the target's proximal edge, although the larger RBE of heavier ions could be also a consideration for treating radioresistant tumors. Table 2 shows the minibeam merging depth in water for planar minibeams of 10-cm range; for pencil minibeams, the depths are 1 to 2 mm longer.

TABLE 1

Dosimetric Considerations

| Target's Proximal depth (cm) | Target's Distal depth (cm) | Recommended Ion Species | Beam Energy (MeV) | FWHM of beam at target's proximal edge(mm) | Recommended beam spacing on-center (mm) | Collimator's transmission |
|---|---|---|---|---|---|---|
| 4 | 8 | H | 102 | 1.6 | 0.7 | 43% |
| 4 | 12 | H | 129 | 1.2 | 0.7 | 43% |
|  |  | He-4 | 512 | 0.6 | 0.6 | 50% |
|  |  | Li-7 | 1,032 | 0.5 | 0.5 | 60% |
| 8 | 16 | Li-7 | 1,214 | 1.1 | 0.7 | 43% |

TABLE 2

Depth of merging in water for planar beams of 10-cm range

| Beam spacing on-center (mm) | Incident beam thickness (mm) | Merging depth for H-1, He-4, and Li-7, respectively (mm) |
|---|---|---|
| 0.5 | 0.3 | 21, 35, 41 |
| 0.7 | 0.3 | 25, 41, 49 |
| 1.2 | 0.3 | 37, 60, 70 |
| 1.2 | 0.5 | 37, 59, 69 |

Comparison Between X-Ray Grid Therapy and Proton Minibeam Therapy

As indicated above in the discussion of the mechanistic bases for the tissue-sparing effect of minibeams and minibeams, the skin-sparing effect of Grid Therapy was based on the dose-volume effect. The method, used with orthovoltage machines, involved positioning of a metal grid with 2-20 mm sized holes on the patient's chest to avoid severe skin damage during radiation therapy. However, for two reasons the tissue-sparing effect of proton minibeams formed in accordance with the present disclosure is much more substantial than that of x-ray Grid Therapy. First, it uses much smaller minibeams, namely 0.3 mm instead of 2-20 mm. Second, the proton minibeams stay minibeams for several centimeters depth in the body and spare all that tissue. This is different from the grid therapy segmented x-ray beams that not only have only a mild skin sparing effect caused by the dose-volume effect, but also quickly broaden further with tissue depth because of the large penumbra effect of the x-ray source, and therefore has no sizable sparing effect in tissue depth. Again, as indicated in the discussion of the mechanisms of the minibeams' tissue-spring effect the effect caused not only by the dose-volume effect but also by the "prompt microscopic biological repair" of very small beams, and this is why it is so robust. On the other hand, Grid therapy spares only the skin and that is only because of the dose-volume effect. Finally, as indicated above the robust tissue-sparing of the proton minibeams for the depth of ~2.5 cm should lead to the sparing of the frontal cortex as well as that of the cortex's gray matter layer; such sparing of the central nervous system will have major ramifications in terms of the brain's function and the patient's cognitive and neurological well-being.

Some of the clinical advantages of the methods formed in accordance with the present disclosure include the following.

Sparing the skin.

Sparing the cortex, including the frontal cortex.

Reducing the number of dose fractions from 30 in the conventional proton therapy to below five or six. This reduction in the number of dose fractions, called hypofractionation, occurs because the patient can be administered with a higher dose in each treatment session because proton minibeams increase the tolerance of the skin and shallow tissues to the proton dose.

Treating larger and/or deeper tumors in the chest and abdomen that respond better to hypofractionation. Because large elapsed times between radiation sessions can help larger tumors to recover to some extent, using larger dose fractions in large tumors is always beneficial. Because treatment of large and/or deep tumors require higher entrance doses, the method can be beneficial because it allows the skin and shallow normal tissues to better tolerate the larger incident doses required to treat these tumors.

Treating tumors of the head and neck. These tumors are difficult to treat not only because they are often radioresistant, requiring large doses to be controlled, but they are often residing near radiosensitive organs such as the parotid glands. The proposed method will be beneficial for both these effects. First, it allows the delivery of much higher dose to the tumor in each session. Second, in treating tumors residing behind shallow, radiosensitive organs, which are not thicker than ~2.5 cm, such as the parotid glands, proton minibeams can go through that organ without damaging it.

While the invention has been particularly shown and described with reference to specific embodiments, it should be apparent to those skilled in the art that the foregoing is illustrative only and not limiting, having been presented by way of example only. Various changes in form and detail may be made therein without departing from the spirit and scope of the invention. Therefore, numerous other embodiments are contemplated as falling within the scope of the present invention as defined by the accompanying claims and equivalents thereto.

What is claimed is:

1. A method for delivering therapeutic radiation to a target volume of a subject, wherein the target volume is located at a predetermined depth, the predetermined depth being measured from an irradiated portion of a surface of the skin of the subject, the method comprising:
   selecting a species of light ions for forming an array of minibeams directed at the target volume based on the predetermined depth;
   selecting a predetermined energy of the species of light ions for confining the therapeutic radiation within the target volume such that the Bragg peak corresponding to the predetermined energy of the species is at a distal side of the target volume;
   delivering the therapeutic radiation to the target volume, including:
      forming the array of minibeams directed at the target volume, the minibeams comprising the species of light ions at the predetermined energy, and
      irradiating a portion of the surface of the skin with the array, the array comprising parallel, spatially distinct minibeams at the surface of the skin in an amount and spatially arranged and sized to maintain a tissue-sparing effect from the surface of the skin to a proximal edge of the target volume and to merge into a solid beam at the proximal edge of the target volume, wherein the species of light ions is selected such that the minibeams broaden and merge into the solid beam at the proximal edge of the target volume to deliver a therapeutic dose of radiation to at least a portion of the target volume; and
   wherein forming the array further includes selecting a gap between adjacent minibeams in the array to maintain the solid beam at the predetermined energy of the species of light ions at the proximal edge.

2. The method of claim 1, wherein the step of delivering the therapeutic dose further includes spreading the Bragg-peak of the light ions forming the minibeams by stepwise lowering the predetermined energy of the light ions across a range of energies to produce a uniform dose distribution throughout the target volume, and wherein the step of selecting the gap includes selecting the gap for which the solid beam is maintained at the proximal edge for each of the energies across the range of energies.

3. The method of claim 2, wherein the energies of the light ions forming the minibeams are between about 10 MeV and 1000 MeV per nucleon.

4. The method of claim 1, wherein the light ions forming the minibeams are protons.

5. The method of claim 1, wherein the array of minibeams is a two-dimensional array of pencil minibeams.

6. The method of claim 5, further comprising shaping a cross-section of the two-dimensional array to substantially match a cross-sectional shape of the target volume.

7. The method of claim 1, wherein the species of light ions forming the minibeams are selected from the group consisting of deuterons and ions of helium, lithium, beryllium, and boron.

8. The method of claim 1, further comprising providing a light ion source and a collimator downstream of the light ion source for forming the array of minibeams on the surface, wherein the gap between the adjacent beams is adjusted by adjusting a spacing of slits in the collimator.

9. The method of claim 8, wherein the collimator is spaced apart from the surface of the skin.

10. The method of claim 1, wherein a width of each of the minibeams at the surface is between 0.1 mm and 0.6 mm.

11. The method of claim 10, wherein the width is about 0.3 mm.

12. The method of claim 1, wherein a cross-sectional profile of the minibeams is one of a circular, square, rectangular, elliptical, and polygonal shape.

13. The method of claim 1, wherein the gap between the minibeams is between about 0.1 mm and about 3.0 mm.

14. The method of claim 1, wherein the gap between the minibeams is between about 0.1 mm and about 1.0 mm.

15. The method of claim 1, wherein the array of minibeams is a one-dimensional array of planar minibeams.

16. The method of claim 1, further comprising additionally performing the steps of selecting a species of light ions, selecting a predetermined energy, and delivering the therapeutic radiation from a second direction, a second portion of the surface of the skin being irradiated from the second direction, the predetermined depth of the target volume being measured from the second portion of the skin.

17. The method of claim 16, wherein the step of delivering the therapeutic dose from the second direction further includes spreading the Bragg-peak of the selected light ions forming the minibeams on the second portion of the skin by stepwise lowering the predetermined energy across a range of energies to produce a uniform dose distribution throughout the target volume, and wherein the gap between adjacent minibeams of an array irradiating the second portion is selected to maintain a solid beam at a proximal edge relative to the second direction for each of the energies across the range of energies.

18. A method for delivering therapeutic light ion radiation to a target volume of a subject, wherein the target volume is located at a predetermined depth, the predetermined depth being measured from an irradiated portion of the skin of the subject, the method comprising:
   irradiating a portion of a surface of the skin with an array of light ion minibeams comprising parallel, spatially distinct minibeams at the surface in an amount and spatially arranged and sized to maintain a tissue-sparing effect from the surface of the skin to a proximal side of the target volume, and to merge into a solid beam at the proximal side of the target volume; and
   wherein a gap between adjacent parallel, spatially distinct minibeams at the surface and a species of light ions forming the minibeams are selected based on a depth of the target volume from the surface.

19. The method of claim 18, wherein a species of light ions forming the light ion minibeams is selected from the group consisting of protons, deuterons, and ions of helium, lithium, beryllium, and boron.

20. The method of claim 19, the method further comprising spreading the Bragg-peak of the species of light ions forming the minibeams by stepwise adjusting the predetermined energy of the light ions across a range of energies to produce a uniform dose distribution throughout the target volume, and wherein the species of light ions and the gap are selected so that the minibeams broaden and merge into the solid beam at the proximal side for each of the energies across the range of energies.

* * * * *